US009999718B2

(12) United States Patent
Brady et al.

(10) Patent No.: US 9,999,718 B2
(45) Date of Patent: Jun. 19, 2018

(54) VOLUME MONITORING DEVICE UTILIZING LIGHT-BASED SYSTEMS

(71) Applicant: Osprey Medical, Inc., Minnetonka, MN (US)

(72) Inventors: Dale Brady, New Brighton, MN (US); Dustin Kasel, Minnetrista, MN (US); Rodney L. Houfburg, Prior Lake, MN (US)

(73) Assignee: OSPREY MEDICAL, INC., Minnetonka, MN (US)

( * ) Notice: Subject to any disclaimer, the term of this patent is extended or adjusted under 35 U.S.C. 154(b) by 89 days.

(21) Appl. No.: 14/222,331

(22) Filed: Mar. 21, 2014

(65) Prior Publication Data

US 2014/0288422 A1    Sep. 25, 2014

Related U.S. Application Data

(63) Continuation-in-part of application No. 13/975,052, filed on Aug. 23, 2013, which is a
(Continued)

(51) Int. Cl.
*A61M 5/00* (2006.01)
*A61M 5/315* (2006.01)
(Continued)

(52) U.S. Cl.
CPC ........ *A61M 5/007* (2013.01); *A61M 5/31568* (2013.01); *A61M 5/31573* (2013.01);
(Continued)

(58) Field of Classification Search
CPC ...... A61M 2205/3306; A61M 5/31568; A61M 5/31571; A61M 5/3157
See application file for complete search history.

(56) References Cited

U.S. PATENT DOCUMENTS

| 3,469,578 A | 9/1969 | Bierman |
| 3,543,759 A | 12/1970 | McWhorter |

(Continued)

FOREIGN PATENT DOCUMENTS

| DE | 19643813 A1 | 4/1998 |
| EP | 0 523 343 A1 | 1/1993 |

(Continued)

OTHER PUBLICATIONS

PCT International Search Report and Written Opinion in International Application PCT/US2013/054510, dated Dec. 4, 2013, 16 pgs.

(Continued)

*Primary Examiner* — Bradley J Osinski
*Assistant Examiner* — Nilay Shah

(57) ABSTRACT

An apparatus includes a syringe housing and a plunger slidably received within the syringe housing between a first position and a second position. The plunger has a substantially opaque portion and a substantially translucent portion. A light sensor module is disposed on the syringe housing. The light sensor module has a light sensor housing and a first sensor element and a second sensor element. The first sensor element and the second sensor element are disposed within the sensor housing. Positioning the plunger at the first position aligns the substantially translucent portion with the first sensor element and positioning the plunger at the second position aligns the substantially translucent portion with the second sensor element.

10 Claims, 14 Drawing Sheets

Related U.S. Application Data continuation-in-part of application No. 13/839,771, filed on Mar. 15, 2013, now Pat. No. 9,320,846.

(60) Provisional application No. 61/694,137, filed on Aug. 28, 2012.

(51) Int. Cl.
   A61M 5/145 (2006.01)
   A61M 5/168 (2006.01)

(52) U.S. Cl.
   CPC ......... A61M 5/1452 (2013.01); A61M 5/1684 (2013.01); A61M 2205/18 (2013.01); A61M 2205/3306 (2013.01); A61M 2205/3379 (2013.01); A61M 2205/3389 (2013.01)

(56) References Cited

U.S. PATENT DOCUMENTS

| | | |
|---|---|---|
| 3,556,122 A | 1/1971 | Laerdal |
| 3,572,375 A | 3/1971 | Rosenberg |
| 3,626,978 A | 12/1971 | Hoekstra |
| 3,633,613 A | 1/1972 | Julow |
| 3,661,174 A | 5/1972 | Cripe |
| 3,695,575 A | 10/1972 | Hauser |
| 3,818,929 A | 6/1974 | Braukmann |
| 3,905,382 A | 9/1975 | Waterston |
| 3,941,149 A | 3/1976 | Mittleman |
| 3,985,141 A | 10/1976 | Stanley et al. |
| 4,000,741 A | 1/1977 | Binard et al. |
| 4,006,736 A | 2/1977 | Kranys et al. |
| 4,030,497 A | 6/1977 | Binard et al. |
| 4,044,793 A | 8/1977 | Krueger et al. |
| 4,074,714 A | 2/1978 | Binard et al. |
| 4,077,405 A | 3/1978 | Haerten et al. |
| 4,084,606 A | 4/1978 | Mittleman |
| 4,136,708 A * | 1/1979 | Cosentino ............ A61M 1/1656 137/99 |
| 4,142,525 A | 3/1979 | Binard et al. |
| 4,147,170 A | 4/1979 | Taylor |
| 4,240,430 A | 12/1980 | Binard et al. |
| 4,289,006 A | 9/1981 | Hallengren |
| 4,318,400 A | 3/1982 | Peery et al. |
| 4,329,985 A | 5/1982 | Bonchek |
| 4,381,006 A | 4/1983 | Genese |
| 4,392,847 A | 7/1983 | Whitney et al. |
| 4,403,988 A | 9/1983 | Binard et al. |
| 4,481,008 A | 11/1984 | Kurtz |
| 4,501,291 A | 2/1985 | Siegrist |
| 4,502,502 A | 3/1985 | Krug |
| 4,550,747 A | 11/1985 | Woodworth et al. |
| 4,602,700 A | 7/1986 | Szabo |
| 4,655,746 A | 4/1987 | Daniels et al. |
| 4,671,786 A | 6/1987 | Krug |
| 4,744,786 A | 5/1988 | Hooven |
| 4,755,172 A | 7/1988 | Baldwin |
| 4,758,223 A | 7/1988 | Rydell |
| 4,795,431 A | 1/1989 | Walling |
| 4,813,937 A | 3/1989 | Vaillancourt |
| 4,838,857 A | 6/1989 | Strowe et al. |
| 4,867,743 A | 9/1989 | Vaillancourt |
| 4,997,420 A | 3/1991 | LeFevre |
| 5,059,174 A | 10/1991 | Vaillancourt |
| 5,094,148 A | 3/1992 | Haber et al. |
| 5,167,631 A | 12/1992 | Thompson et al. |
| 5,273,187 A | 11/1993 | Suzuki |
| 5,376,785 A | 12/1994 | Chin et al. |
| 5,460,609 A | 10/1995 | O'Donnell |
| 5,556,386 A | 9/1996 | Todd |
| 5,573,515 A | 11/1996 | Wilson et al. |
| 5,575,767 A | 11/1996 | Stevens |
| 5,662,612 A | 9/1997 | Niehoff |
| 5,685,851 A | 11/1997 | Murphy et al. |
| 5,707,356 A | 1/1998 | Paul |
| 5,785,681 A | 7/1998 | Indravudh |
| 5,792,117 A * | 8/1998 | Brown ............... A61B 5/14532 235/462.04 |
| 5,799,700 A | 9/1998 | Teh et al. |
| 5,800,397 A | 9/1998 | Wilson et al. |
| 5,806,519 A | 9/1998 | Evans, III et al. |
| 5,827,941 A | 10/1998 | Good et al. |
| 5,840,026 A | 11/1998 | Uber, III et al. |
| 5,840,071 A | 11/1998 | Kriesel et al. |
| 5,882,338 A | 3/1999 | Gray |
| 5,882,343 A | 3/1999 | Wilson et al. |
| 5,885,216 A | 3/1999 | Evans, III et al. |
| 5,916,165 A | 6/1999 | Duchon et al. |
| 6,019,747 A | 2/2000 | McPhee |
| 6,086,559 A | 7/2000 | Enk |
| 6,113,578 A | 9/2000 | Brown |
| 6,159,180 A | 12/2000 | Kriesel et al. |
| 6,317,623 B1 | 11/2001 | Griffiths et al. |
| 6,397,098 B1 | 5/2002 | Uber, III et al. |
| 6,409,699 B1 | 6/2002 | Ash |
| 6,442,418 B1 | 8/2002 | Evans, III et al. |
| 6,558,125 B1 | 5/2003 | Futterknecht |
| 6,850,792 B2 | 2/2005 | Ohishi |
| 6,858,020 B2 | 2/2005 | Rusnak |
| 6,866,654 B2 | 3/2005 | Callan et al. |
| 6,889,074 B2 | 5/2005 | Uber, III et al. |
| 6,901,283 B2 | 5/2005 | Evans, III et al. |
| 6,966,893 B2 | 11/2005 | Holtby et al. |
| 6,969,353 B2 | 11/2005 | Brock-Fisher et al. |
| 6,970,735 B2 | 11/2005 | Uber, III et al. |
| 7,022,107 B1 | 4/2006 | Christensen et al. |
| 7,065,395 B2 | 6/2006 | Lienard et al. |
| 7,094,216 B2 | 8/2006 | Trombley, III et al. |
| 7,255,684 B2 | 8/2007 | Zubry |
| 7,270,648 B2 | 9/2007 | Kazemzadeh |
| 7,326,186 B2 | 2/2008 | Trombley, III et al. |
| 7,470,253 B2 | 12/2008 | Kriesel et al. |
| 7,516,760 B2 | 4/2009 | Weber |
| 7,611,503 B2 | 11/2009 | Spohn et al. |
| 7,618,412 B2 | 11/2009 | Chernack |
| 7,678,070 B2 | 3/2010 | Kumar et al. |
| 7,766,885 B2 | 8/2010 | Olsen |
| 7,815,604 B2 | 10/2010 | Massengale et al. |
| 7,854,726 B2 | 12/2010 | Fago et al. |
| 7,925,330 B2 | 4/2011 | Kalafut et al. |
| 7,927,305 B2 | 4/2011 | Yribarren et al. |
| 7,951,129 B2 | 5/2011 | Chinchoy |
| 7,955,301 B1 | 6/2011 | McKay |
| 8,075,490 B2 | 12/2011 | Lofgren et al. |
| 8,147,448 B2 | 4/2012 | Sundar et al. |
| 8,172,790 B2 | 5/2012 | Hunter et al. |
| 8,197,443 B2 | 6/2012 | Sunder et al. |
| 8,197,444 B1 | 6/2012 | Bazargan et al. |
| 8,208,994 B2 | 6/2012 | Niethammer |
| 8,257,310 B2 | 9/2012 | Donovan et al. |
| 8,295,914 B2 | 10/2012 | Kalafut et al. |
| 8,303,547 B2 | 11/2012 | Brown |
| 8,323,267 B2 | 12/2012 | Haase |
| 8,328,758 B2 | 12/2012 | Childers et al. |
| 2001/0039396 A1 | 11/2001 | Kriesel et al. |
| 2002/0128611 A1 | 9/2002 | Kandalaft |
| 2003/0055380 A1 | 3/2003 | Flaherty |
| 2003/0233069 A1 | 12/2003 | Gillespie, Jr. et al. |
| 2004/0135078 A1* | 7/2004 | Mandro ............... A61M 5/145 250/231.13 |
| 2004/0178255 A1 | 9/2004 | Eich et al. |
| 2005/0020983 A1 | 1/2005 | Schreijag et al. |
| 2005/0059931 A1 | 3/2005 | Garrison et al. |
| 2005/0165364 A1 | 7/2005 | DiMatteo et al. |
| 2005/0277912 A1 | 12/2005 | John |
| 2006/0178632 A1 | 8/2006 | Trombley, III et al. |
| 2007/0060820 A1 | 3/2007 | Lofgren et al. |
| 2007/0062250 A1 | 3/2007 | Krulevitch et al. |
| 2007/0093752 A1 | 4/2007 | Zhao et al. |
| 2007/0161970 A1 | 7/2007 | Spohn et al. |
| 2008/0004507 A1 | 1/2008 | Williams, Jr. et al. |
| 2008/0147007 A1 | 6/2008 | Freyman et al. |
| 2008/0154187 A1 | 6/2008 | Krulevitch et al. |
| 2008/0164970 A1 | 7/2008 | Malzahn |

(56) References Cited

U.S. PATENT DOCUMENTS

| | | | |
|---|---|---|---|
| 2008/0287865 A1* | 11/2008 | Nielsen | A61M 5/3155 604/65 |
| 2008/0312536 A1* | 12/2008 | Dala-Krishna | A61B 8/12 600/459 |
| 2009/0234231 A1 | 9/2009 | Knight et al. | |
| 2010/0114064 A1 | 5/2010 | Kalafut et al. | |
| 2010/0211003 A1 | 8/2010 | Sundar et al. | |
| 2010/0274180 A1* | 10/2010 | Donovan | A61B 17/8872 604/65 |
| 2011/0092828 A1 | 4/2011 | Spohn et al. | |
| 2012/0024987 A1 | 2/2012 | Naegele Nacken | |
| 2012/0036937 A1 | 2/2012 | Sprenger et al. | |
| 2012/0041427 A1 | 2/2012 | Caffey et al. | |
| 2012/0116217 A1 | 5/2012 | Lee-Sepsick et al. | |
| 2012/0277661 A1 | 11/2012 | Bernard et al. | |
| 2012/0277667 A1 | 11/2012 | Yodat et al. | |
| 2012/0283186 A1 | 11/2012 | Adams | |
| 2012/0302950 A1 | 11/2012 | Landsman et al. | |
| 2012/0316460 A1 | 12/2012 | Stout | |
| 2013/0261729 A1 | 10/2013 | Gillick et al. | |
| 2014/0066860 A1 | 3/2014 | Houfburg et al. | |
| 2014/0066891 A1 | 3/2014 | Burns et al. | |
| 2014/0163339 A1 | 6/2014 | Goldstein et al. | |
| 2015/0202361 A1 | 7/2015 | Burns et al. | |
| 2015/0202386 A1 | 7/2015 | Brady et al. | |
| 2016/0213834 A1 | 7/2016 | Brady et al. | |

FOREIGN PATENT DOCUMENTS

| | | |
|---|---|---|
| EP | 1930603 A1 | 6/2008 |
| JP | H06 296690 A | 10/1994 |
| WO | WO 84/01718 A1 | 5/1984 |
| WO | WO 89/03230 A1 | 4/1989 |
| WO | WO 96/11024 A1 | 4/1996 |
| WO | WO 98/17974 | 4/1998 |
| WO | 02/064196 | 8/2002 |
| WO | WO 02/098493 A1 | 12/2002 |
| WO | WO 2004/009163 A1 | 1/2004 |
| WO | WO 2005/068848 A1 | 7/2005 |
| WO | WO 2009/039203 A2 | 3/2009 |
| WO | WO 2009/065153 A2 | 5/2009 |
| WO | 2014/035647 | 3/2014 |

OTHER PUBLICATIONS

Cigarroa, et al., "Dosing of Contrast Material to Prevent Nephropathy in Patients with Renal Disease", Am. Jour. of Med., Jun. 1989, pp. 649-652.

Gurm, et al., "Renal Function-Based Dosing to Define Safe Limits of Radiographic Contrast Media in Patients Undergoing Percutaneous Coronary Interventions", JACC, 2011:58:907-14.

Davies, Justin E. et al., "Evidence of a Dominant Backward-Propagating 'Suction' Wave Responsible for Diastolic Coronary Filling in Humans, Attenuated in Left Ventricular Hypertrophy" (Circulation. 2006;113:1768-1778).

PCT International Search Report and Written Opinion in International Application PCT/US2015/021294, dated Jun. 19, 2015, 13 pgs.

PCT International Search Report and Written Opinion in International Application PCT/US2016/025671, dated Jul. 26 2016, 16 pgs.

PCT International Search Report and Written Opinion in International Application PCT/US2016/025302, dated Jul. 20, 2016, 13 pgs.

International Search Report and Written Opinion for Application No. PCT/US2014/052319 dated Feb. 5, 2015.

* cited by examiner

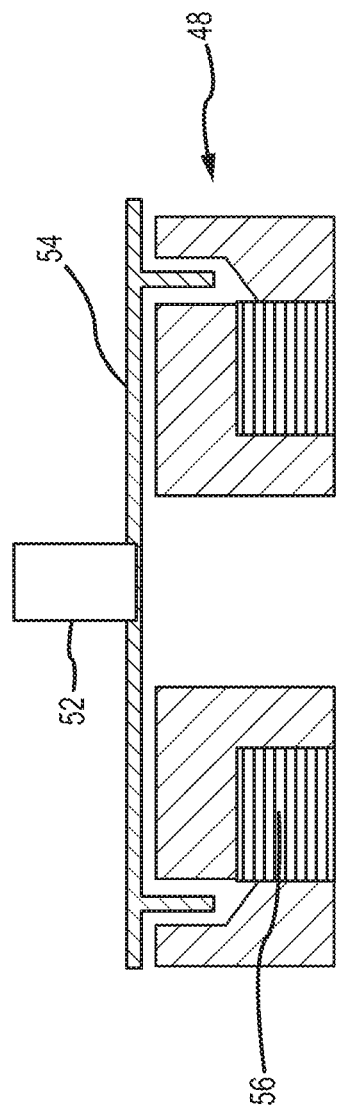

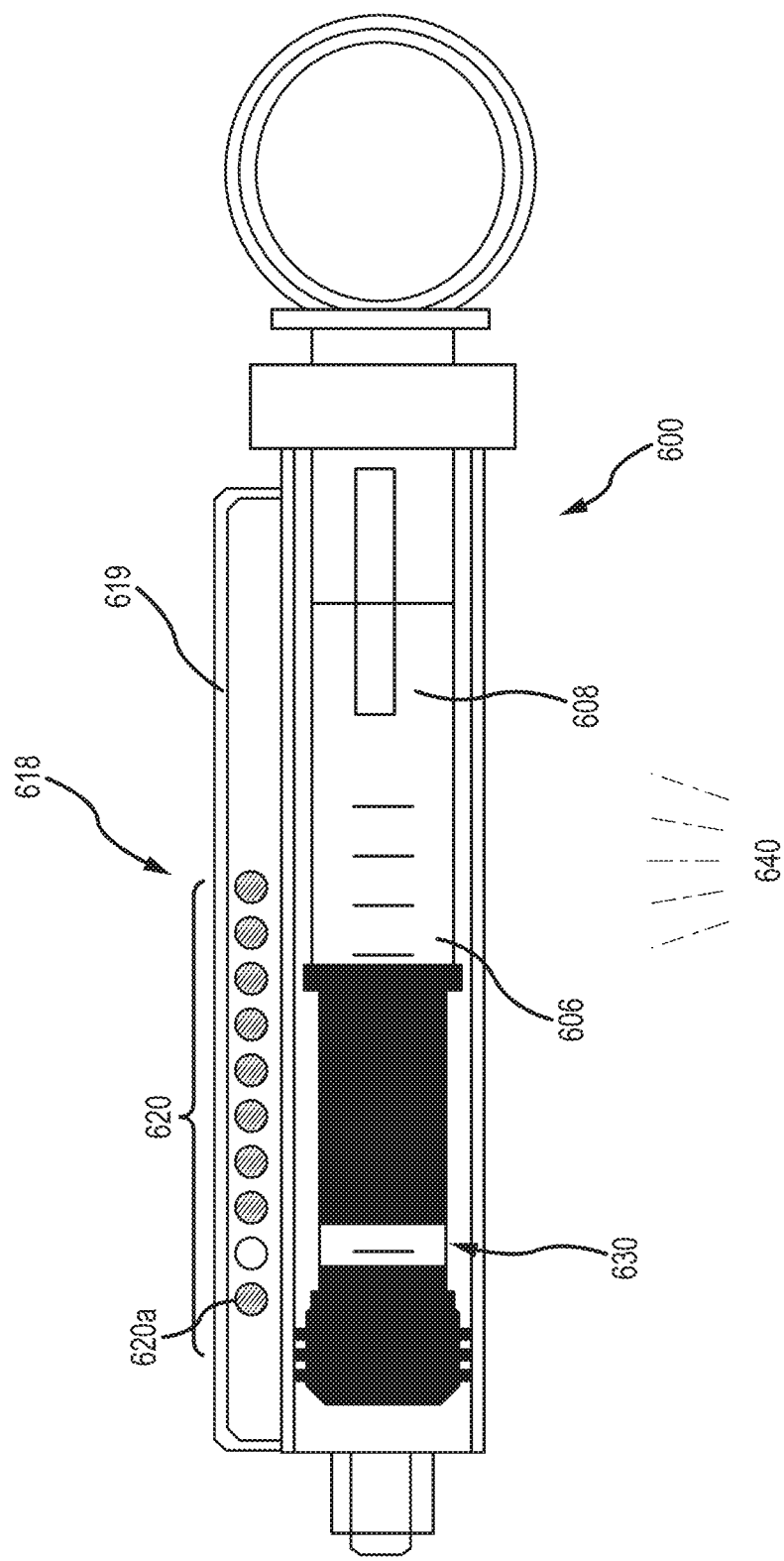

VOLUME MONITORING DEVICE UTILIZING LIGHT-BASED SYSTEMS

CROSS-REFERENCE TO RELATED APPLICATIONS

This application is a continuation-in-part of U.S. patent application Ser. No. 13/975,052, filed Aug. 23, 2013, entitled "Volume Monitoring Device"; which is a continuation-in-part of U.S. patent application Ser. No. 13/839,771, filed Mar. 15, 2013, entitled "Devices and Methods for Modulating Medium Delivery", now U.S. Pat. No. 9,320,846, which claims priority to and the benefit of U.S. Provisional Application Ser. No. 61/694,137, filed Aug. 28, 2012, entitled "Devices and Methods for Modulating Medium Delivery," the disclosures of which are hereby incorporated by reference herein in their entireties.

INTRODUCTION

This disclosure pertains to devices and methods used to control, transform or otherwise modulate the delivery of a substance, such as radiopaque contrast, to a delivery site and/or devices and methods that may be used to measure or otherwise make quantitative assessments of a medium delivered to a delivery site. More specifically, it is the intention of the following devices and methods to modulate and/or assess the delivery of media to a vessel, vascular bed, organ, and/or other corporeal structures so as optimize the delivery of media to the intended site, while reducing inadvertent or excessive introduction of the media to other vessels, vascular beds, organs, and/or other structures, including systemic introduction.

The terms medium (media), agent, substance, material, medicament, and the like, are used generically herein to describe a variety of fluidal materials that may include, at least in part, a substance used in the performance of a diagnostic, therapeutic or/and prophylactic medical procedure and such use is not intended to be limiting.

SUMMARY

This summary is provided to introduce a selection of concepts in a simplified form that are further described below in the Detailed Description. This summary is not intended to identify key features or essential features of the claimed subject matter, is not intended to describe each disclosed embodiment or every implementation of the claimed subject matter, and is not intended to be used as an aid in determining the scope of the claimed subject matter. Many other novel advantages, features, and relationships will become apparent as this description proceeds. The figures and the description that follow more particularly exemplify illustrative embodiments.

In one aspect, the technology relates to an apparatus having: a syringe housing; a plunger slidably received within the syringe housing between a first position and a second position, the plunger having a substantially opaque portion and a substantially translucent portion; and a light sensor module disposed on the syringe housing, wherein the light sensor module has a light sensor housing and a first sensor element and a second sensor element, wherein the first sensor element and the second sensor element are disposed within the sensor housing, wherein positioning the plunger at the first position aligns the substantially translucent portion with the first sensor element and positioning the plunger at the second position aligns the substantially translucent portion with the second sensor element. In an embodiment, the apparatus has a lead extending from the light sensor. In another embodiment, the apparatus includes an interface for connecting the lead to a measuring device, and wherein the measuring device displays a total volume injected and emits a warning of a critical outcome. In yet another embodiment, the light sensor housing is releasably fixed to the syringe housing. In still another embodiment, the apparatus includes means for releasably securing the light sensor housing to the syringe housing.

In another embodiment of the above aspect, the means includes at least one of a clamp, a clasp, a hook and loop fastener, and a magnet. In an embodiment, the apparatus further includes a light emitter module disposed on the syringe housing, wherein the light emitter module has a light emitter housing and a first emitter element and a second emitter element, wherein the first emitter element and the second emitter element are disposed within the emitter housing. In another embodiment, positioning the plunger at the first position aligns the substantially translucent portion with the first emitter element and positioning the plunger at the second position aligns the substantially translucent portion with the second emitter element. In yet another embodiment, the first emitter element and the first sensor element are aligned. In still another embodiment, the sensor housing is disposed on the syringe housing about 180 degrees from the sensor housing.

In another aspect, the technology relates to an apparatus having: a syringe housing; a plunger slidably received within the syringe housing; a light sensor module secured to the syringe housing; and a light emitter module secured to the syringe housing, wherein the plunger has a plurality of substantially translucent portions. In an embodiment, the plurality of substantially translucent portions includes: a first portion having a first translucency; and a second portion having a second translucency less than the first translucency. In another embodiment, the plurality of substantially translucent portions includes a gradation. In yet another embodiment, the light sensor module incudes a plurality of light sensors and the light emitter module includes a plurality of light emitters. In still another embodiment, the light emitter module is disposed at a location about the syringe housing at least about 90 degrees from the light sensor module.

In yet another aspect, the technology relates to a method of determining a condition of a syringe, the method including receiving a first signal from a first light sensor, wherein a position of the first light sensor on the syringe is known. In an embodiment, the method includes determining a first position of a piston disposed within the syringe based at least in part on the received first signal. In another embodiment, the method further includes emitting a light signal from a light emitter disposed on the syringe. In yet another embodiment, the method further includes receiving a second signal from a second light sensor, wherein a position of the second light sensor on the syringe is known. In still another embodiment, the method further includes determining a second position of the piston based at least in part on the received second signal.

BRIEF DESCRIPTION OF THE DRAWINGS

There are shown in the drawings, embodiments which are presently preferred, it being understood, however, that the technology is not limited to the precise arrangements and instrumentalities shown.

FIG. 1D depicts a side sectional view of the brake mechanism of the exemplary synchronized agent delivery arrangement of FIG. 1C.

FIGS. 5A-5C depict embodiments of a monitoring syringe.

DETAILED DESCRIPTION

Figure 1A:
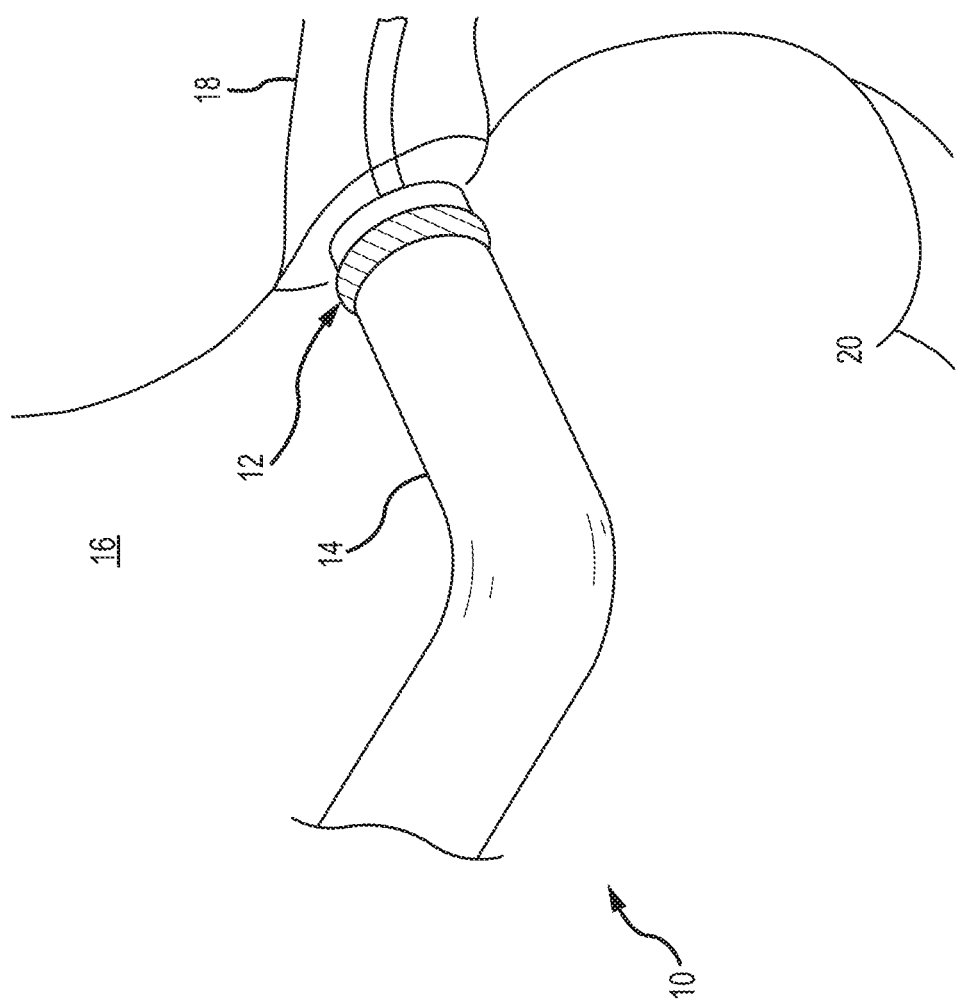
FIG. 1A depicts an exemplary synchronized agent delivery with indirect modulation, adjacent a distal portion of a treatment system therefor.

There are numerous occasions in the diagnostic, prophylactic and treatment practice of medicine wherein an agent, medicant, or medium is preferably delivered to a specific site within the body, as opposed to a more general, systemic introduction. One such exemplary occasion is the delivery of contrast media to coronary vasculature in the diagnosis (i.e., angiography) and treatment (i.e., balloon angioplasty and stenting) of coronary vascular disease. The description, as well as the devices and methods described herein, may be used in modulating and/or monitoring medium delivery to the coronary vasculature in prevention of toxic systemic effects of such an agent. One skilled in the art, however, would recognize that there are many other applications wherein the controlled delivery and/or quantitative assessment of a media to a specific vessel, structure, organ or site of the body may also benefit from the devices and methods disclosed herein. For simplicity, these devices and methods may be described as they relate to contrast media delivery modulation and/or measurement. As such, they may be used in the prevention of Contrast Induced Nephropathy; however, it is not intended, nor should it be construed, so as to limit the use to this sole purpose. Exemplary other uses may include the delivery, injection, modulation, or measurement of: cancer treatment agent to a tumor, thrombolytic to an occluded artery, occluding or sclerosing agent to a vascular malformation or diseased tissue; genetic agent to a muscular bed, neural cavity or organ, emulsion to the eye, bulking agent to musculature and/or sphincter, imaging agent to the lymphatic system, antibiotics to an infected tissue, supplements in the dialysis of the kidney, to name but a few.

Example—Prevention of Contrast Induced Nephropathy

Contrast Induced Nephropathy (CIN) is a form of kidney damage caused by the toxic effects of dyes (radiopaque contrast media) used, for example, by cardiologists to image the heart and its blood vessels during commonly performed heart procedures, such as angiography, angioplasty, and stenting. In general, the dye is toxic and is known to damage kidneys. Although most healthy patients tolerate some amount of the "toxicity," patients with poorly or non-functioning kidneys may suffer from rapidly declining health, poor quality of life, and significantly shortened life expectancy. Potential consequences of CIN include: irreversible damage to the kidneys, longer hospital stays, increased risk of heart disease, increased risk of long-term dialysis, and ultimately, a higher mortality risk. For patients who acquire CIN, their risk of dying remains higher than others without CIN, and this risk can continue up to five years after their procedure. CIN has a significant economic burden on the healthcare system and currently there is no treatment available to reverse damage to the kidneys or improper kidney performance, once a patient develops CIN.

To date, there have been attempts in reducing the toxic effects of contrast media on patients who undergo procedures involving dyes, especially those patients who are at high risk for developing CIN. Some of these efforts have been to: change the inherent toxicity (of a chemical or molecular nature) of the dyes, reduce the total amount of contrast agent injected (through injection management and/or dye concentration), and remove media through coronary vasculature isolation and blood/contrast agent collection systems, to name a few. These methods and devices used in the control of the toxic effects of contrast agents have had their inherent compromises in effectively delivering a contrast media specifically to a target site while minimizing the systemic effects. As an example, changing the composition of a dye and/or injection concentration may help reduce a contrast agent's inherent toxicity at the expense of the contrast agent's ability to perform its intended function (e.g., visualization of vasculature). Conversely, the ability to "collect" contrast agent laden blood "downstream" from the visualization site may ensure visualization, but requires the complexity of placement and operation of a collection system.

Other attempts to manage the amount of contrast agent delivered to a patient have employed automated, powered (versus manual, syringe-injected) contrast media injection systems. Close monitoring and control of the total quantity of contrast agent injected may have a positive impact in reducing the incidence of CIN. However, these injection systems are expensive (including capital equipment and disposables), cumbersome to use within a cath lab, and take additional time and expertise to set up and operate properly. Improper use could negate any benefits seen by better management of the quantity of the contrast agent delivered to a patient, and the additional time required to set up such a system may also add significant complexity to a procedure. The devices and methods described herein may measure or otherwise quantitatively assess the amount of medium injected or delivered to a delivery site using a relatively fast, simple, economical, and safe system.

The measurement systems described herein may be employed as a system of quantitative assessment or in combination with a modulator. Additional systems are described in U.S. patent application Ser. No. 13/839,771, the disclosure of which is hereby incorporated by reference herein in its entirety. FIGS. 1A-1D depict embodiments where a modulator is constructed so as to measure the amount of an agent delivered from the system. Conversely, FIG. 2, for example, describes the use of a measurement system for the quantitative assessment of the volume of medium delivered and the inherent analysis of the total volume delivered versus some predetermined critical amount, such as the Gurm ratio, whether or not it is used with a modulator.

It should be understood that measurements may be performed prior to a medium being modulated, simultaneously with modulation, or after the modulation process, if desired. Further, it is also contemplated that the measurement devices and methods may be used with any of the modulation systems, such as described in U.S. patent application Ser. No. 13/839,771. Moreover, the embodiments described herein are exemplary in nature and should not be construed as limiting the various combinations possible.

Some embodiments of control and modulation devices disclosed herein may send and/or receive a sensor signal so as to coordinate a valving, controlling, or otherwise modulating function on an injection agent before the agent enters an intended target injection site. Modulation may include, for example, valving (or otherwise modulating) an injection dispensed from an injection device. As described in U.S. patent application Ser. No. 13/839,771, indirect valving (or otherwise controlling mechanisms) may be proximally or distally positioned within, about, and/or upon the agent delivery system. An example of an indirect modulation control system 10 is depicted in FIGS. 1A-1D. In this example, a sensor 12 is deployed distally on a delivery catheter 14 (as seen in FIG. 1A) and a modulating device 30 (of FIG. 1B) is provided proximally. The sensor 12 of FIG. 1A is an exemplary pressure sensor positioned on the distal tip of the delivery catheter 14. As described previously, this is only one example of a type of sensor that may be used in obtaining a signal to synchronize the delivery of medium with the blood flow rate. Moreover, FIG. 1A illustrates the positioning of the sensor 12 upon the distal tip of the delivery catheter 14 within the aorta 16 to the left coronary artery 18, off the aortic root 20. The exemplary positioning of the sensor 12 in FIG. 1A should not be limited to that shown in order to perform the functions described herein, since there may be a multitude of sensor types (and commensurate signals) positioned at various locations on (i.e., as a function of respiration), through (i.e., as a function of imaging) and within the body (i.e., as a function of a variable proximate a target delivery site). Clearly, even the placement of a distal pressure sensor in exemplary FIG. 1A could take many forms, such as: a pressure wire alongside the catheter, a lumen within the catheter body for pressure measurement, a pressure sensor deployed within the distal tip of the catheter, and a pressure sensor deployed distally of the distal tip of the catheter and into the target vessel, to name but a few.

Figure 1B:
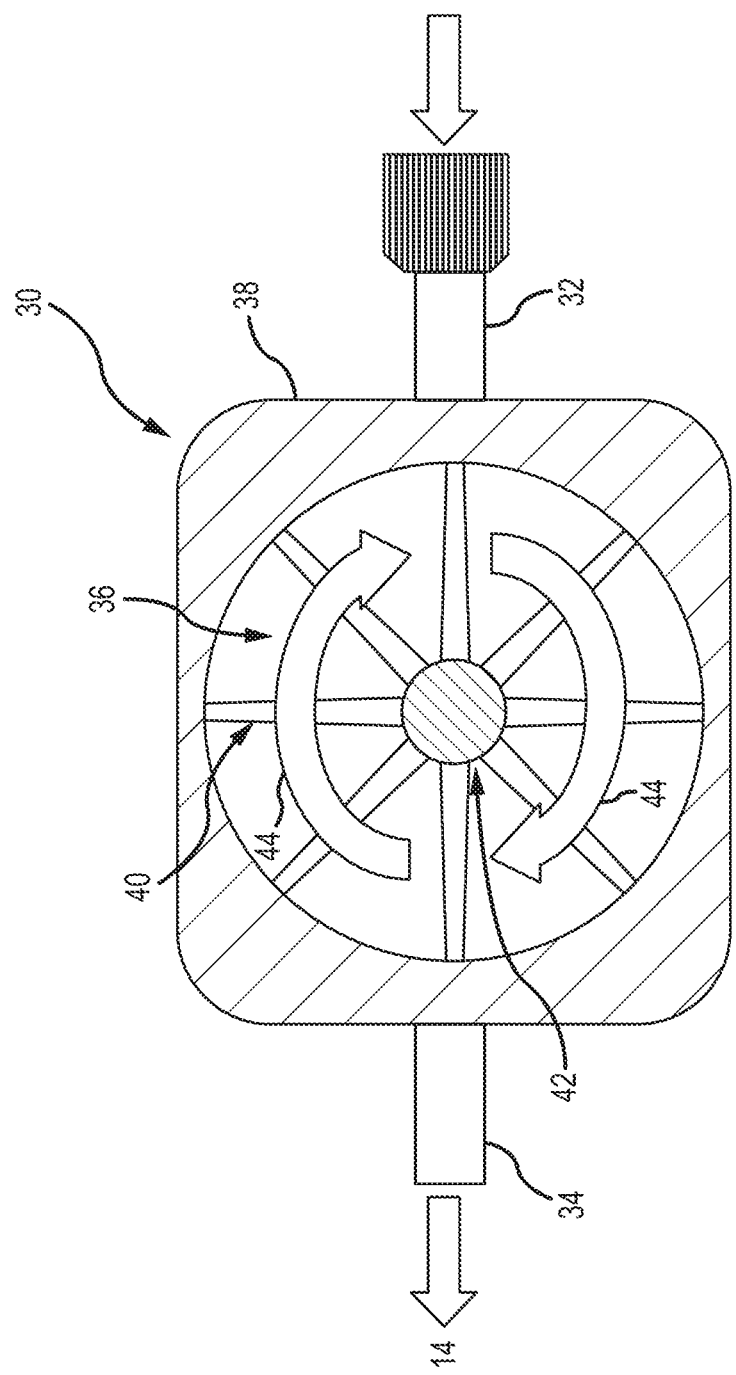
FIG. 1B depicts a top view of an exemplary synchronized agent delivery with indirect modulation, adjacent a proximal portion of such a treatment system.

Referring to FIG. 1B, modulating device 30 may include an inlet port 32 (from the injection device) and an outlet port 34 (to the delivery catheter 14). The flow of injection fluid may pass through the injection port 32 and into a fluid chamber 36 within a body or housing 38 of the modulator 30. The modulator 30 may have a plurality of vane/plates 40 attached to a cylindrical hub 42 disposed within the fluid chamber 36. The vanes 40 and hub 42 may be formed to define a "pinwheel" structure of vane-hub that is capable of rotating freely (relative to fluid chamber 36 and body 38 of modulator 30) upon the injection of medium into the fluid chamber 36 through the injection port 32. The hub 42 may be designed to preferentially rotate in one direction. For example, FIG. 1B illustrates the preferential flow of fluid and rotation of the vane-hub, in a clockwise direction, via flow arrows 44. From the fluid chamber 36, injection fluid may flow out of the modulator 30 via the outlet port 34.

One advantage of the vane-hub modulator 30 depicted in FIG. 1B is that it may be easy to measure, or otherwise identify, the total volume of injection fluid delivered through the modulating device 30 (over time) since the volume of fluid passing through the device 30 during one rotation of the vane 40 or hub 42 may be easily determined, and the number of rotations simply counted by a counting mechanism. Alternatively, each "cell" of fluid between adjacent vanes 40 may be readily counted by a counting mechanism. The counting mechanism may include a magnetic, mechanical, ultrasonic, infrared or similar measurement device capable of identifying the number of times a vane 40 and/or some other element of the device 30 has passed within its field of measurement, or by determining the number of times the axis of the hub 42 has rotated. The output of such a counting mechanism may be utilized to determine and display (in real time) the total volume of medium used during a procedure. Advantageously, in the management of medium injected, an operator or physician may readily see the amount of medium used (as determined by the counting mechanism and presented by a suitable display or indicative output). The determination of the volume (via calculations or conversions based on, for example, counted rotations) may be performed as part of the counting device, or may be performed by a display device. In addition to providing volume measurements, the counting mechanism, signal, or display may incorporate various algorithms to alert the operator before or when maximum volume of agent has been administered (based upon an operator-determined value, Maximum Acceptable Contrast Dose, Gurm ratio, etc.). For example, the Maximum Acceptable Contrast Dose index, as described by Cigarroa, et al. (June 1989) "Dosing of Contrast Material to Prevent Nephropathy in Patients with Renal Disease" Am Jour of Med. 649-652, suggests that a maximum amount of contrast injected (in mL) be equal to 5 mL× body weight (Kg)/Baseline Serum Creatinine level (in mg/dL). In another example, the maximum amount of contrast injected (in mL) as described in Gurm, et al. "Renal Function-Based Dosing to Define Safe Limits of Radiographic Contrast Media in Patients Undergoing Percutaneous Coronary Interventions" JACC 2011:58:907-14, suggests that the maximum contrast used (in mL) should be less than, or equal to, 2 if it is divided by a calculated Creatinine Clearance (mL/min) of the patient. Regardless of the indicator utilized, the system may include a display that not only provides total volume used, but also warns the operator of use as compared to one or more indicators of a maximum administration.

Figure 1C:
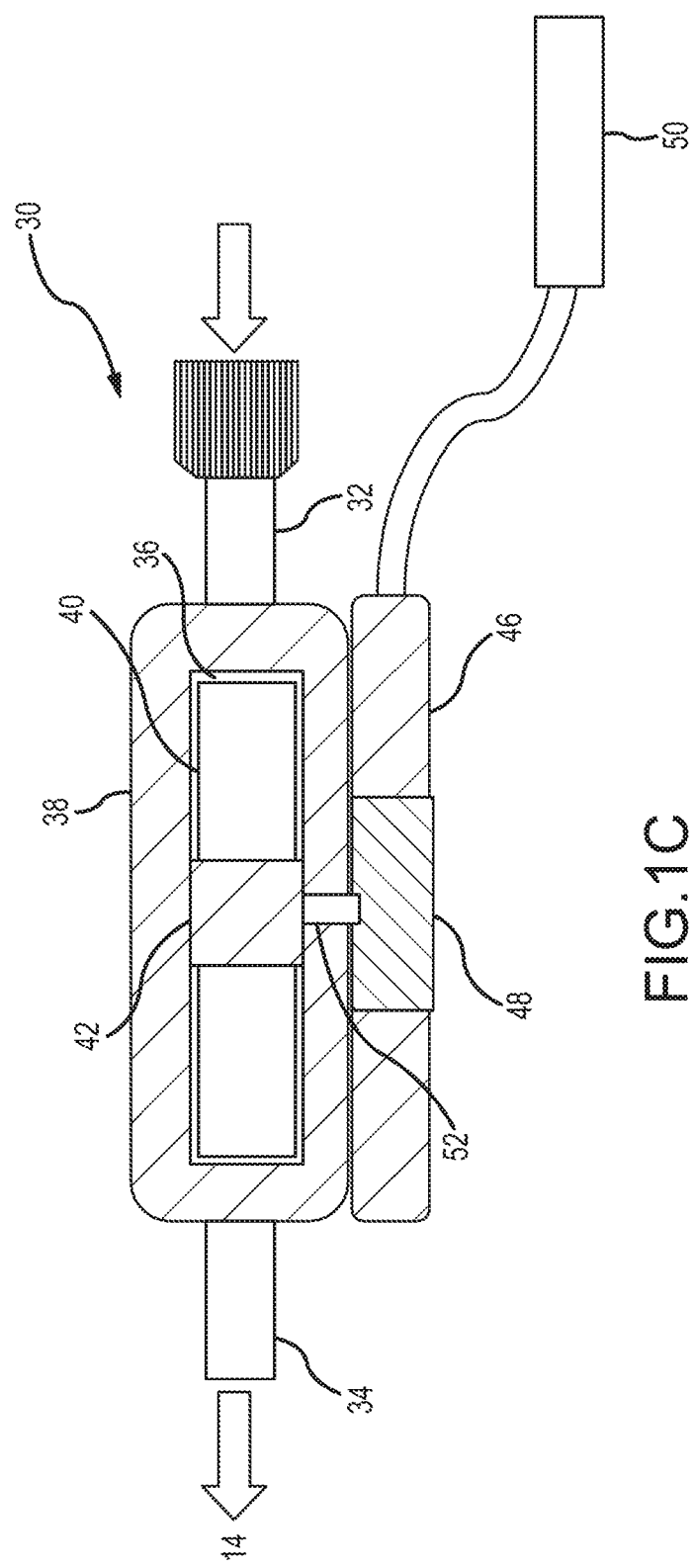
FIG. 1C depicts a side view of an exemplary synchronized agent delivery with indirect modulation, adjacent a proximal portion of such a treatment system.

Continuing with the description of the exemplary modulation device 30 shown in FIGS. 1B-1C, the vane-hub modulator 30 may include two components. The first, the body 38 (described above) may be situated adjacent a controller/actuator 46 and may include the input port 32, the output port 34 and the fluid chamber 36 with rotating vane 40 and hub 42. The body 38 may come into contact with bodily fluids and, accordingly, may be disposable. The controller/actuator 46 may also include a brake mechanism 48, sensor signal, receiver 50, and the like may be used to clutch, brake, or otherwise inhibit the rotation of the hub 42 so as to provide resistance to rotation. The resistance induced to the rotation may be coordinated with a signal from sensor 12 of FIG. 1A, so as to modulate an injection from an injector to improve an agent fluid flow.

The braking, or clutching, of the modulator 30 of FIG. 1C may be performed through a variety of mechanisms, to include, for example, mechanical, hydromechanical, electromechanical, electromagnetic, chemomechanical, etc. FIG. 1C illustrates one such mechanism 48 for braking a shaft 52 of the hub 42, using electromagnetic force. The exemplary braking structure 48 is further detailed in FIG. 1D, wherein the longitudinal shaft 52 of the hub 42 is coupled to a hysteresis plate or disc 54 positioned within a magnetic coil 56. When electricity is applied to the magnetic coil 56, a magnetic flux is transferred to the hysteresis disc 54 (as it passes through the field) causing a magnetic "drag" on the disc 54. The drag, or braking, applied to the hysteresis disc 54 (and thus the shaft 52 of the hub 42) may be increased or decreased with increasing or decreasing voltage applied to the magnetic field to modulate the flow of medium as intended. When electrical current is removed, the connected disc 54 may rotate freely about an axis of shaft 52. Upon modulating, braking mechanism 48 of FIG. 1D may increase the drag (reduce the flow rate) of the agent as needed to improve the flow profile of the agent or fluid.

FIGS. 1A-AD describe one system to regulate the flow profile and determine the volume of injection agent through a modulator, and as such, are intended to illustrate the modulation monitoring, control, and measurement concepts disclosed herein without limitation. Therefore, this embodiment is but one example how one might use a modulator device and a measurement device to control the delivery of an agent, as well as measure the amount of agent delivered.

Other embodiments including devices and methods in quantitative assessment, or otherwise measurement, of the volume of delivery of an agent are described below. It is to be understood that these measurement devices may also be used in combination with a variety of agent modulators and the description is intended to be exemplary and not limiting.

Figure 2:
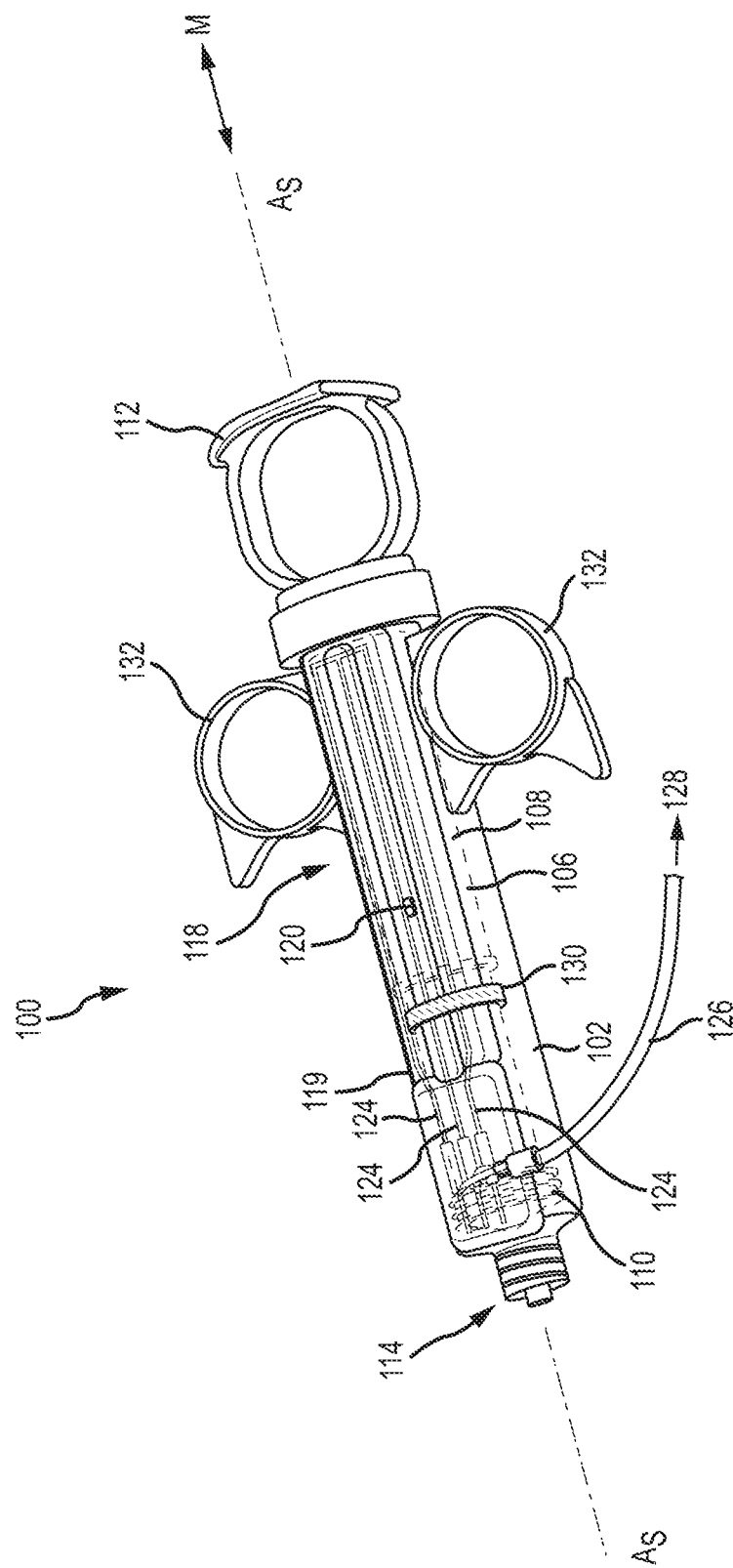
FIG. 2 depicts a perspective view of an embodiment of a monitoring syringe.
Figure 3:
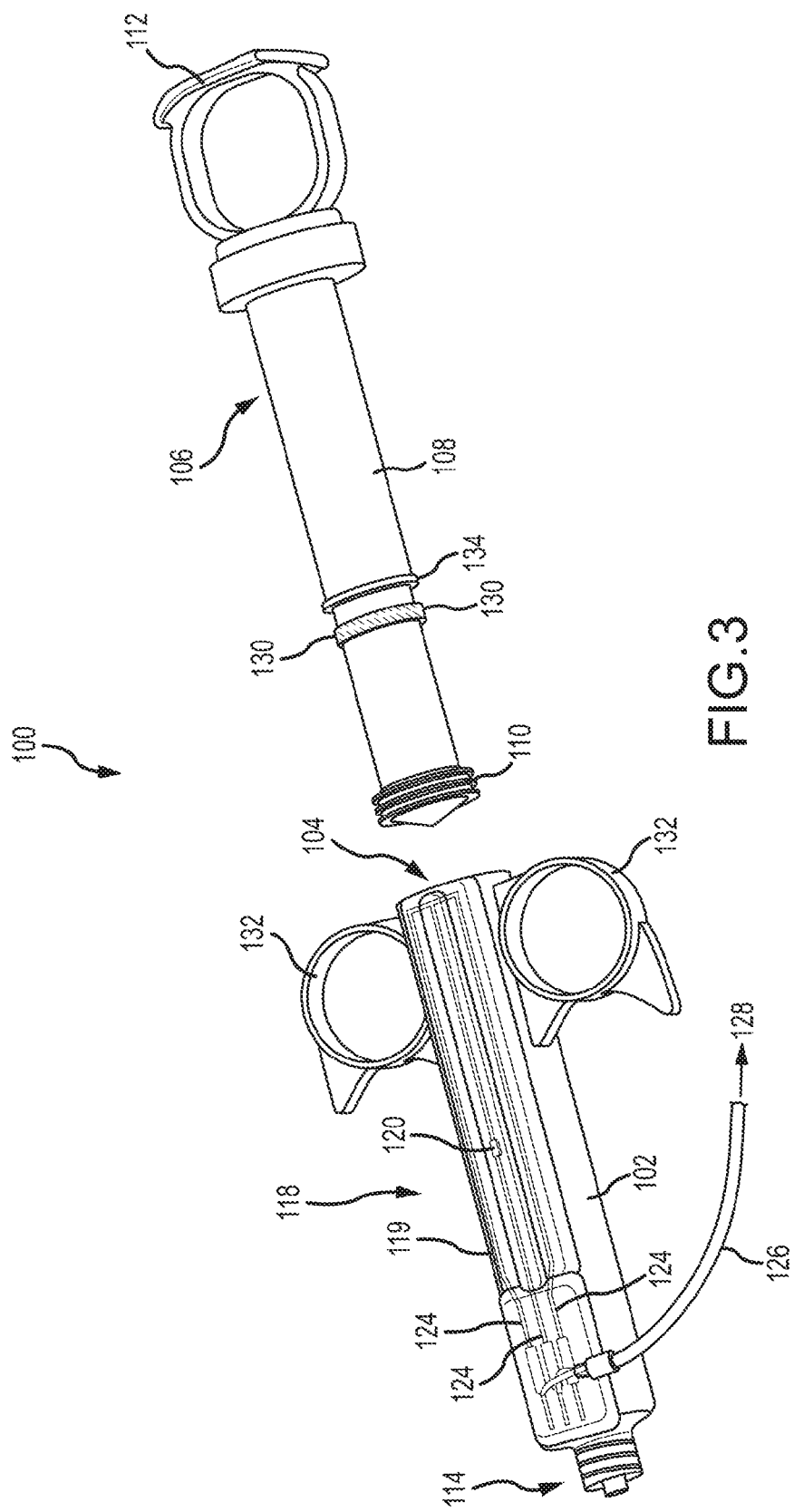
FIG. 3 depicts a partially exploded perspective view of the monitoring syringe of FIG. 2.

FIGS. 2 and 3 depict a perspective view and a perspective exploded view, respectively, of a monitoring syringe 100. The monitoring syringe 100 includes a syringe housing 102 (or chamber) defining an inner bore 104. A plunger 106 including a shaft 108 and a piston 110 is slidably received in the bore 104. More specifically, the piston 110 is slidably engaged with an interior surface of the bore 104 and linear movement M of the shaft 108 within the bore 104 moves the piston 110. Movement M is along the syringe axis $A_S$. The plunger 106 is moved back and forth within the bore 104 by the movement of a thumb pad, such as a thumb-ring 112, as described in more detail below. As the plunger 106 is moved M in a direction towards the discharge end 114 of the syringe housing 102, the fluid contained therein is discharged into a tube or needle (not shown) and delivered to a patient. Note that throughout the description a cylindrical-type chamber 102 and inner bore 104 are described; however, it is contemplated that there may be a variety of constructions of a housing/bore 102/104 and plunger 106 that provide the function as anticipated herein and the shape (including rectangular, ovular, triangular cross-section, etc.), in and of itself, should not be limiting.

In the depicted embodiment, a light sensor module 118 is secured to an exterior surface of the syringe housing 102. The light sensor module 118 includes a light sensor housing 119 that encloses a light sensor 120. In certain embodiments, the light sensor 120 may be a linear array comprising a plurality of pixels, such as model no. TSL1406R manufactured by AMS-TAOS USA, Inc., of Plano, Tex. In other embodiments, the light sensor 120 may be one or more discrete light sensors, such as photoresistors. In general, a greater number of discrete light sensor elements (pixels, photoresistors, or otherwise), may improve accuracy. One or more leads or wires 124 extend from an end of the light sensor module 118, as required or desired for a particular application. However, one skilled in the art would readily recognize that wires 124 need not be utilized with different sensor configurations. For example, using a light sensor on a circuit board may require alternative connections. A cable 126 connects at an end 128 to an interface unit that analyzes the output of the light sensor module 118 and provides this information to a user of the monitoring syringe 100, typically on a display. In other embodiments, communication may be via a radio, Bluetooth, of other wireless connection. The displayed information may include volume of the chamber, volume remaining, volume dispensed, fluid type, flow rate, fluid pressure or temperature and/or other information, as required or desired for a particular application.

In the depicted embodiment, the shaft 108 of the plunger 106 is substantially translucent, meaning light may generally pass through the shaft 108. A discrete portion or band 130 may be disposed on or formed with the shaft 108. The band 130, in this case, is a portion of the shaft 108 having a translucency less than the translucency of the remainder of shaft 108, or an opacity greater than the opacity of the remainder of the shaft. As the plunger 106 is slidingly moved M along the axis $A_S$, the band 130 of lesser transparency passes in front of the light sensor 120 of the light sensor element 118. Light passes through the plunger portion having higher translucency and is received by the light sensor module 118. The light sensor module 118 sends a signal to the interface unit that determines the position of the plunger 106 within the syringe housing 102, based on the opacity of band 130 along the light sensor 120. Thus, the position of the plunger 106 can be determined. The interface may also determine the various types of information listed above, based on a known diameter and length of the bore 104 of the syringe housing 102. Two finger rings or tabs 132 receive the fingers of a user during use. A stop 134 prevents the plunger 106 from being pulled out of the syringe housing 102.

Figure 4A:
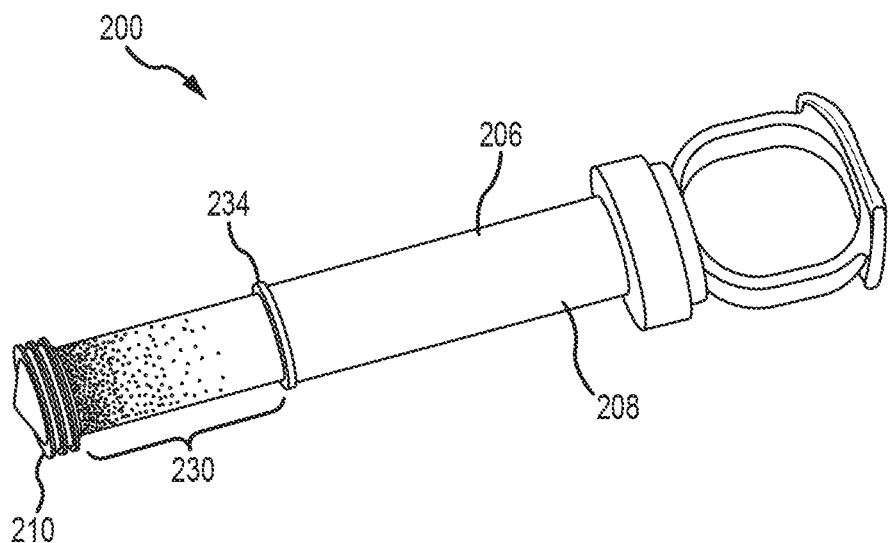
FIGS. 4A-4C depict partial enlarged perspective views of other embodiments of monitoring syringes.
Figure 4B:
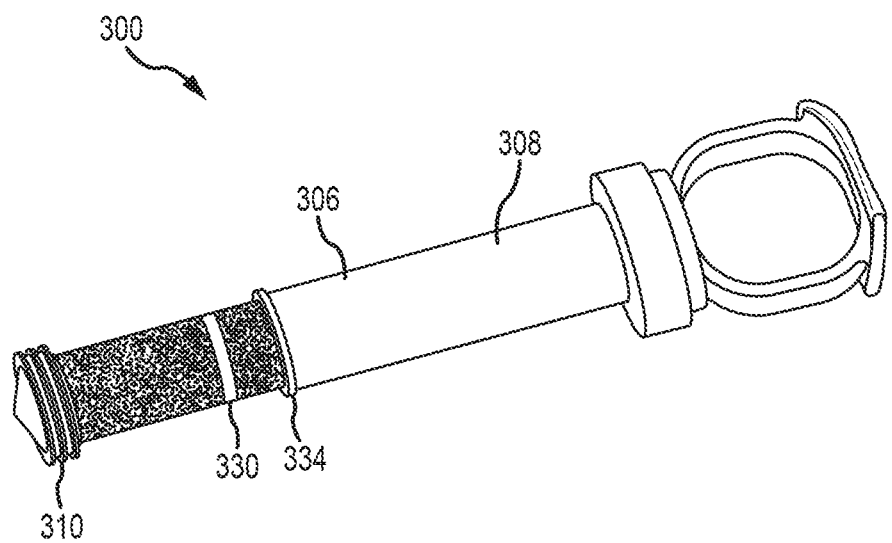
Figure 4C:
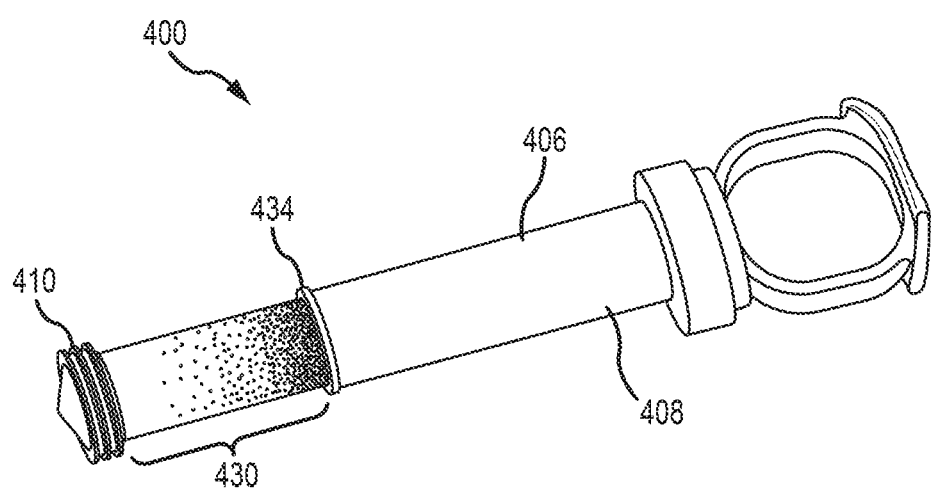

FIGS. 4A-4C depict various alternative configurations of plungers that may be utilized with various monitoring syringes herein. FIG. 4A depicts a partial enlarged perspective view of another embodiment of a monitoring syringe 200. In this embodiment, a plunger 206 includes a shaft 208. Rather than the discrete band depicted above in FIGS. 2 and 3, the depicted embodiment includes a gradation 230 of varying translucency/opacity along the plunger shaft 208. In the depicted embodiment, the gradation 230 is darker (i.e., less translucent or more opaque) proximate the piston 210. Proximate the stop 234, the translucency of the gradation 230 is higher (and conversely, the opacity lower). The transition of the gradation may be smooth or in discrete bands. In certain embodiments such as the one depicted in FIG. 4A, no shading may be present proximate the stop 234 and the translucency of that portion may be the same as that of the shaft 208, generally.

FIG. 4B depicts a partial enlarged perspective view of another embodiment of a monitoring syringe 300. In this embodiment, a plunger 306 includes a shaft 308. Rather than the discrete higher opacity band depicted above in FIGS. 2 and 3, the depicted embodiment utilizes a shaft 308 having a discrete band 330 of higher translucency. That is, the portion of the shaft 330 disposed between the piston 310 and stop 334 is substantially opaque, while the band 330 is substantially translucent.

FIG. 4C depicts a partial enlarged perspective view of another embodiment of a monitoring syringe 400. In this embodiment, a plunger 406 includes a shaft 408. The gradation 430 is disposed opposite the gradation of the embodiment of FIG. 4A. In the embodiment of FIG. 4C, the gradation 430 is darker (i.e., less translucent or more opaque) proximate the stop 434. Proximate the piston 410, the translucency of the gradation 430 is higher. The transition of the gradation 430 may be smooth or in discrete bands. In certain embodiments, no shading may be present proximate the piston 410 and the translucency of that portion may be the same as that of the shaft 408, generally.

Any of the configurations of the plungers depicted in FIG. 2, 3, or 4A-4C may be utilized with the monitoring syringes depicted herein. That is, plungers having discrete bands of opacity or translucency, or plungers having increasing or decreasing gradations (measured from the piston to the stop) may be utilized with syringes utilizing light sensor modules. Regardless of plunger opacity/translucency configuration, the light sensor modules detect changes of light being received as the monitoring syringe is used. Depending on the location of one or more light sensors within the light sensor module, the changes enable an interface device to determine the position of the plunger and, accordingly, the volume and other characteristics or conditions of the device.

The various embodiments of measuring syringes of FIGS. 2-4C describe devices that generally include a light sensor module and/or light sensor positioned on, in, or proximate the device housing or bore. The portion of the device including the variation of translucency is principally positioned on, in, or proximate the device plunger. Of course, the configuration of the components can be reversed if desired, such that the housing/bore includes variations in translucency, while the plunger includes a light sensor or light sensor module. These embodiments are also considered within the scope of the technology.

Figure 5B:
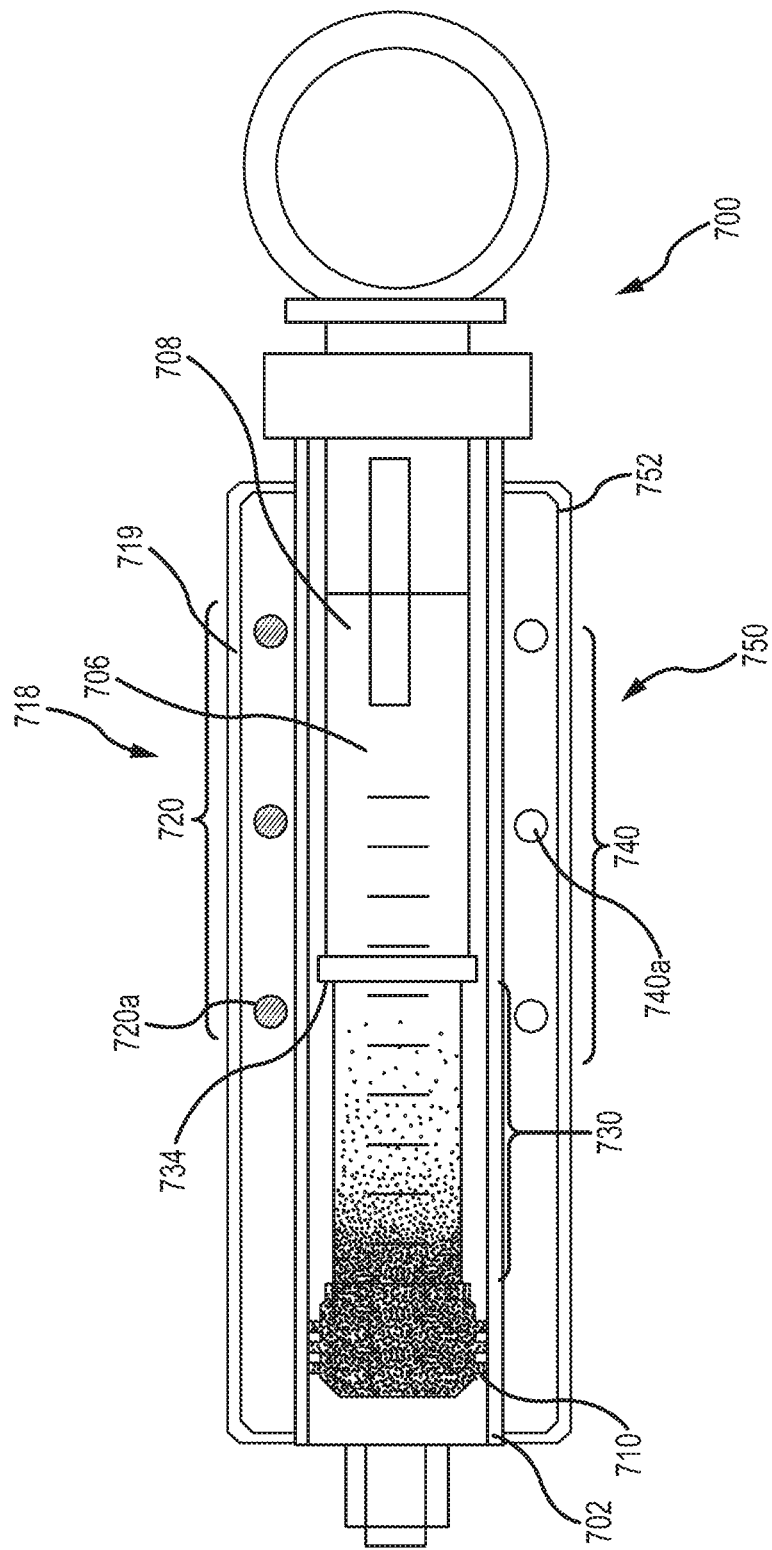
Figure 5C:
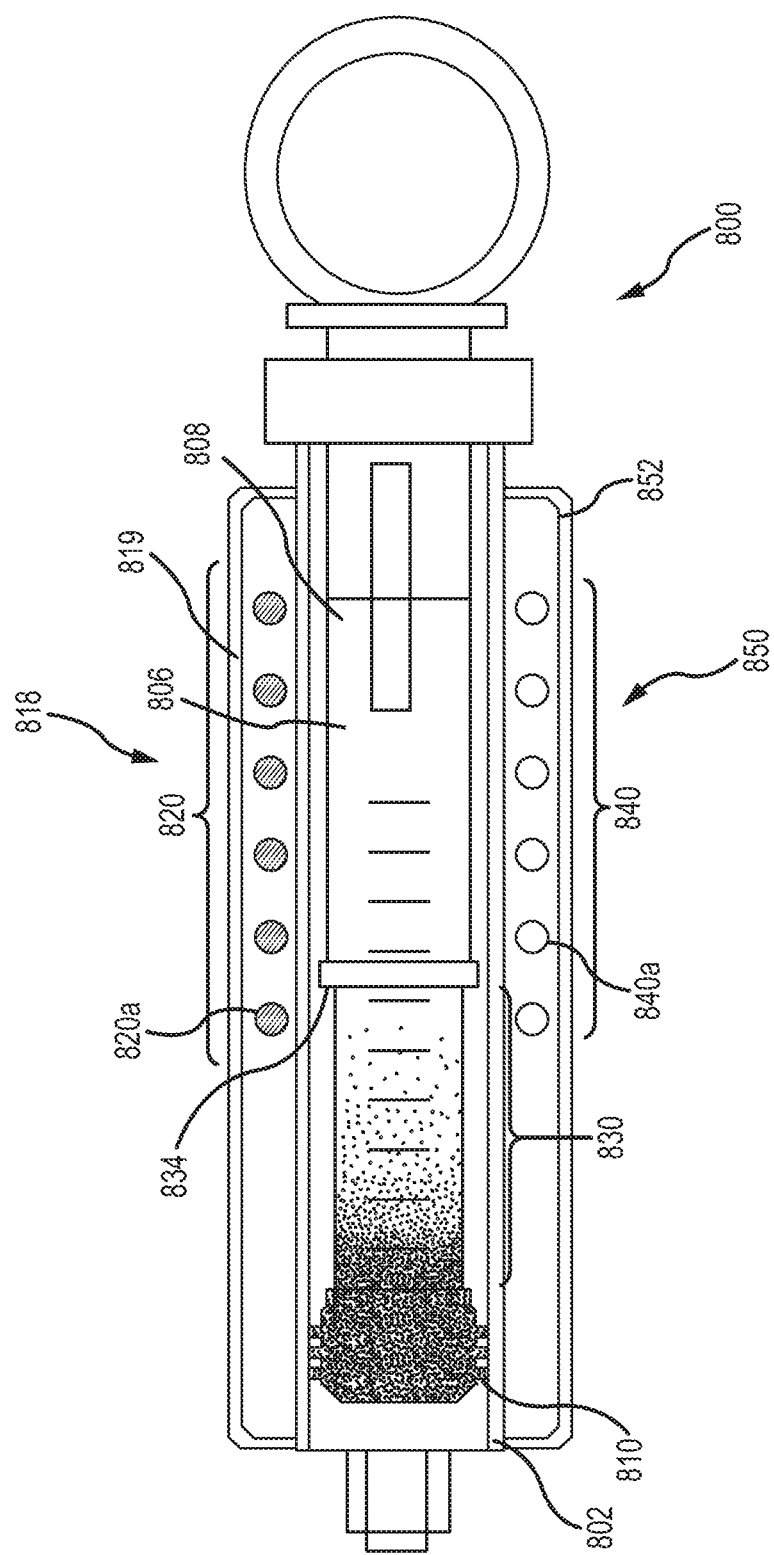

FIGS. 5A-5C depict various embodiments of monitoring syringes. FIG. 5A depicts a monitoring syringe 600 utilizing a sensor module 618. The sensor module 618 includes a sensor housing 619 and a linear array 620. The linear array 620 includes a plurality of pixels 620a. In the depicted embodiment, the monitoring syringe 600 includes a plunger 606 having a shaft 608 including a translucent band 630. The band 630 need not be completely translucent, but merely sufficiently translucent such that the pixels 620a within the light array 620 may detect a change in light received. In this embodiment, the received light is ambient light 640 that may be present in a room such as a surgical suite. Conversely, light source 640 may be from a source other than ambient light, such as an infrared or ultraviolet light generator, for example. Additionally, the light sensor module 618 may be configured with filters to receive light of only a predetermined wavelength (e.g., infrared, ultraviolet, etc.). Alternatively, the plunger 606 or shaft 608 may be configured with a filter to filter the received light to the desired wavelength.

FIG. 5B depicts a monitoring syringe 700 utilizing a sensor module 718. The sensor module includes a sensor housing 719 and a light sensor 720 that includes discrete light sensor elements 720a, such as for example, photoresistors. In the depicted embodiment, the monitoring syringe 700 includes a plunger 706 having a shaft 708 including a gradation 730, wherein the gradation 730 is less translucent proximate the piston 710 and more translucent proximate the stop 734. Instead of utilizing ambient light as with the previous embodiments, the monitoring syringe of FIG. 5B utilizes a light emitter module 750, such as, for example, light emitting diodes (LEDs). The light emitter module 750 is secured to the syringe housing 702 in a manner similar to the light sensor module 718. The light emitter module 750 includes an emitter housing 752 and a light emitter 740 including a plurality of light emitter elements 740a. In the depicted embodiment, the discrete light emitter elements 740a may be disposed opposite and aligned with the discrete light sensor elements 720a, but this is not required. Additionally, the light emitter elements 740a may be configured to only emit light having a particular wavelength, or the light may be filtered so as to restrict the light that is emitted and/or sensed. As the gradation 730 passes between the light sensor module 718 and the light emitter module 750, light signals are received by the discrete light sensor elements 720a. The light sensor module 718 sends signals to an interface, which processes the signals to determine the position of piston 710. The light sensor module 718 and light emitter module 750 are disposed approximately 180 degrees from each other about the circumference of the syringe housing 702. In other embodiments, the modules 718, 750 may be disposed less than about 180 degrees from each other. In certain embodiments, the modules 718, 750 may be disposed about 90 degrees from each other. If desired, the modules 718, 750 may be contained in a common housing.

FIG. 5C depicts a monitoring sensor 800 utilizing a sensor module 818. The sensor module includes a sensor housing 819 and a light sensor 820 that includes discrete light sensor elements 820a, such as photoresistors. In the depicted embodiment, the monitoring syringe 800 includes a plunger 806 having a shaft 808 including a gradation 830, wherein the gradation 830 is less translucent proximate the piston 810 and more translucent proximate the stop 834. The monitoring syringe 800 utilizes a light emitter module 850. The light emitter module 850 is secured to the syringe housing 802 in a manner similar to the light sensor module 818. The light emitter module 850 includes an emitter housing 852 and a light emitter 840 including a plurality of light emitter elements 840a. Note that the emitter housing 852 and sensor housing 819 may include a structural element (e.g., tape or adhesive) to facilitate fixation of emitters/sensors to the chamber, or may include emitters/sensors being disposed within the chamber wall. In the depicted embodiment, the discrete light emitters 840a are disposed opposite and aligned with the discrete light sensor elements 820a, but this is not required. Additionally, the light emitter elements 840a may be configured to only emit light having a particular wavelength (for example, near infrared light generator), or may be filtered. As the gradation 830 passes between the light emitter module 818 and the light sensor module 850, light signals are received by the discrete light sensor elements 820a. The light sensor module 818 sends signals to an interface, which processes the signals to determine the position of piston 810. The light sensor module 818 and light emitter module 850 are disposed approximately 180 degrees from each other about the circumference of the syringe housing 802. In other embodiments, the modules 818, 850 may be disposed as described above with regard to FIG. 5B. The monitoring syringe 800 of FIG. 5C utilizes a light sensor module 818 and light emitter module 850 having higher sensor and emitter densities than those of FIGS. 5A and 5B. As described above, this may result in greater positional accuracy.

Figure 6:
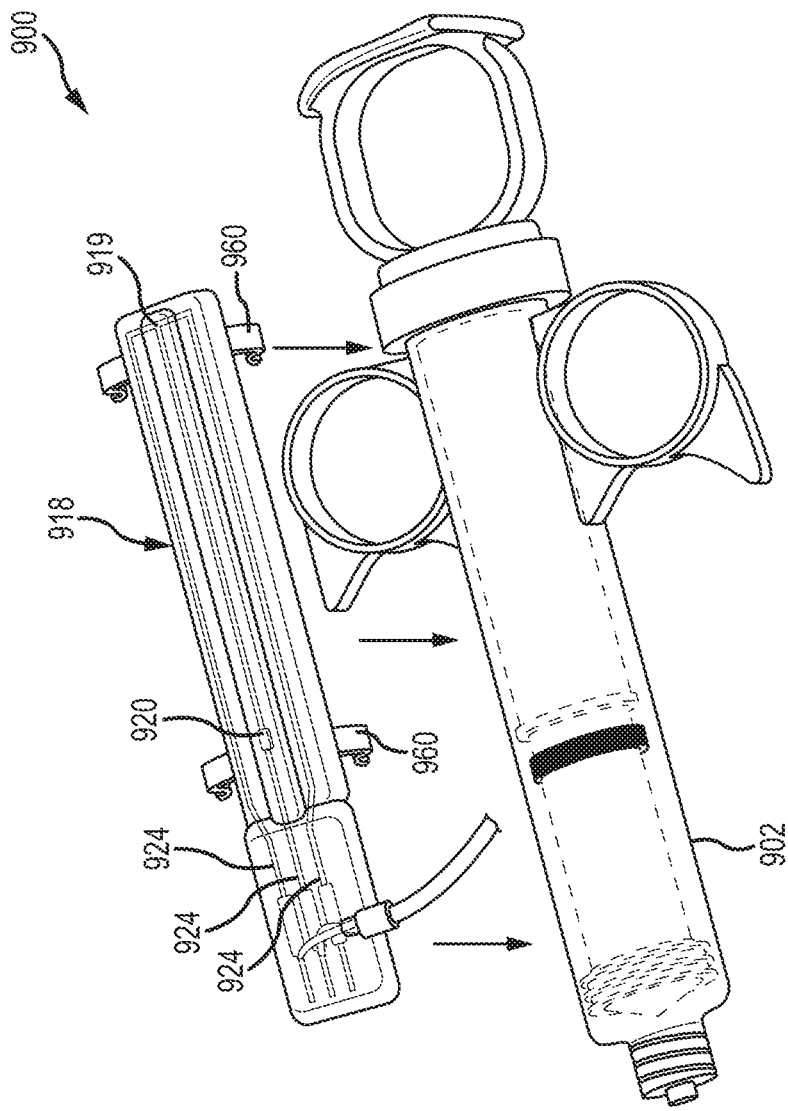
FIG. 6 depicts a partially exploded perspective view of another embodiment of a monitoring syringe.

FIG. 6 depicts another embodiment of a monitoring syringe 900. In this case, the light sensor housing 919, containing the light sensor 920 and wires 924, is detachably secured to the syringe housing 902. The light sensor housing 919 may be secured with clips, C-clamps, resilient catches, or other elements 960 that allow the light sensor housing 919 to be removed from the syringe housing 902. Such a configuration may be desirable so the light sensor housing 919 and related components may be reused on a different syringe, typically after a medical procedure. The light sensor housing 919 may be removed from a first syringe housing 902 and reattached to a second syringe housing at a later time. Once the wires 924 (or similar connective instruments)

are reconnected to the interface (as described above) a calibration program may be executed so as to calibrate the light sensor module 918 for the new syringe.

The embodiments described herein may include various elements or components to measure and/or detect a displacement of a plunger within a chamber, such as a syringe. And, with the detection of a positional relationship of a plunger within a chamber, a user may explicitly or implicitly determine a volume of media that may have been ejected from a chamber. Some of the embodiments described may include various sources in the generation of light, as well as components to detect or sense the light, depending on the positional relationship of the plunger/piston and the chamber. Other alternative embodiments capable of identifying positional relationships of a plunger and chamber (and changes thereof) may include, without limitation, the following technologies. A hall sensor (coiled wire along syringe axis) may be placed on, or in proximity to, the chamber with a magnet attached to the plunger (so as to act as a variable proximity sensor). Multiple low sensitivity hall sensors may be disposed along the chamber of the syringe with a magnet attached to the plunger. Laser light may be emitted and detected to determine a positional relationship of the plunger along the chamber axis. An absolute encoder may be used to "read" the direct displacement of the plunger.

Figure 7:
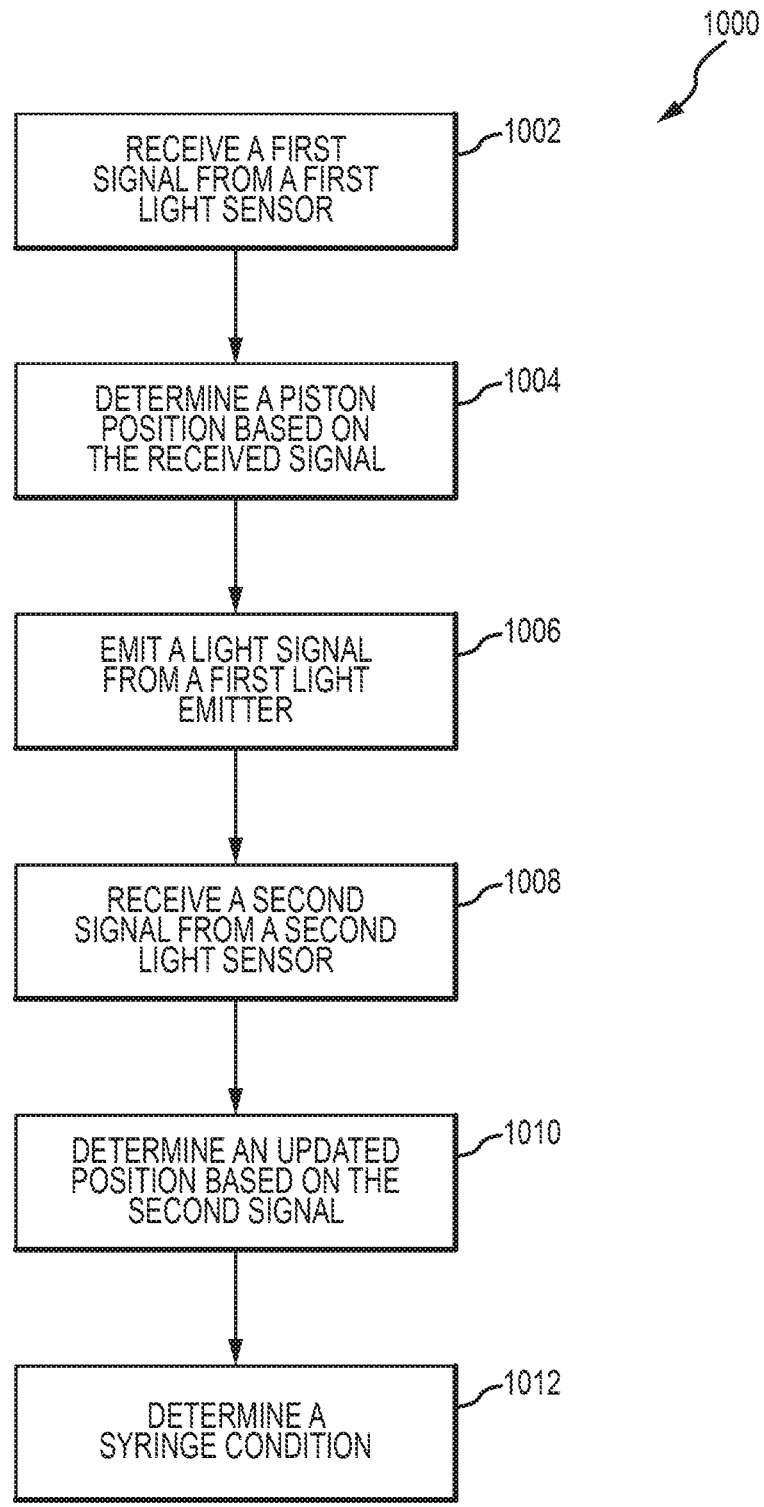
FIG. 7 depicts a method of using a monitoring device.

FIG. 7 depicts a method 1000 of using a monitoring syringe utilizing light signals. At operation 1002, a signal is received from a light sensor, the position of which on a monitoring syringe is known. Other characteristics of the light sensor, such as receptive wavelength, may be known. Based on the position of the light sensor and the signal received from said sensor, a position of a piston is then determined in operation 1004. In certain embodiments of the method 1000, a light signal is emitted from the first emitter in operation 1006. In embodiments where multiple light sensors are used, a light signal may be received at a second light sensor having known characteristics (e.g., position) in operation 1008. An updated position may then be determined based on the characteristic of the second light sensor and the signal in operation 1010. At any time a light signal is received from a known light sensor, a condition of the syringe (such as those described herein) may be determined, as in operation 1012.

Figure 8:
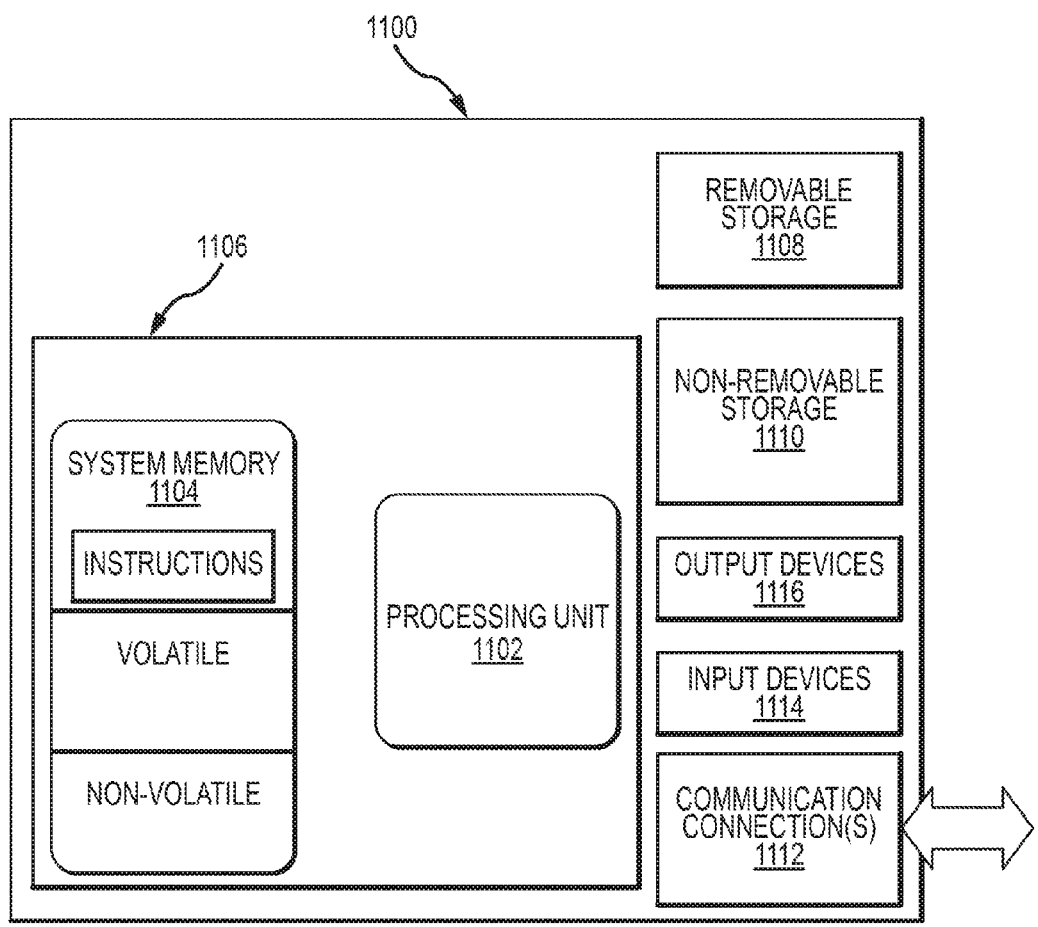
FIG. 8 depicts one example of a suitable operating environment in which one or more of the present examples may be implemented.

FIG. 8 illustrates one example of a suitable operating environment 1100 in which one or more of the present embodiments may be implemented. This is only one example of a suitable operating environment and is not intended to suggest any limitation as to the scope of use or functionality. Other well-known computing systems, environments, and/or configurations that may be suitable for use include, but are not limited to, personal computers, server computers, hand-held or laptop devices, multiprocessor systems, microprocessor-based systems, programmable consumer electronics such as smart phones, network PCs, minicomputers, mainframe computers, smartphones, tablets, distributed computing environments that include any of the above systems or devices, and the like.

In its most basic configuration, operating environment 1100 typically includes at least one processing unit 1102 and memory 1104. Depending on the exact configuration and type of computing device, memory 1104 (storing, among other things, instructions to perform the monitoring methods described herein) may be volatile (such as RAM), non-volatile (such as ROM, flash memory, etc.), or some combination of the two. This most basic configuration is illustrated in FIG. 8 by dashed line 1106. Further, environment 1100 may also include storage devices (removable, 1108, and/or non-removable, 1110) including, but not limited to, magnetic or optical disks or tape. Similarly, environment 1100 may also have input device(s) 1114 such as touch screens, keyboard, mouse, pen, voice input, etc. and/or output device(s) 1116 such as a display, speakers, printer, etc. Also included in the environment may be one or more communication connections, 1112, such as LAN, WAN, point to point, Bluetooth, RF, etc.

Operating environment 1100 typically includes at least some form of computer readable media. Computer readable media can be any available media that can be accessed by processing unit 1102 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 1100 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media. Such networking environments are commonplace in offices, enterprise-wide computer networks, intranets and the Internet. In some embodiments, the components described herein comprise such modules or instructions executable by computer system 1100 that may be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 1100 is part of a network that stores data in remote storage media for use by the computer system 1100.

The monitoring systems described herein may be utilized to deliver any types of fluids to a patient during a medical procedure. Such fluids may include medium (media), agents, substances, materials, medicaments, and the like. It should be noted that these terms are used generically herein to describe a variety of fluidal materials that may include, at least in part, a substance used in the performance of a diagnostic, therapeutic or/and prophylactic medical procedure and such use is not intended to be limiting. It should be understood that the medium delivery modulation and/or measurement devices and methods described herein are not limited to the particular, representative embodiments as described, since variations may be made to these embodiments without departing from the scope and spirit of the disclosure. Likewise, terminology employed in the description of embodiments is not intended to be limiting and is used merely for the purpose of conveyance of the concept. Unless defined otherwise, all technical and scientific terms used herein have the same meaning as commonly understood to one of ordinary skill in the art of which the disclosed devices and methods pertain.

The materials utilized in the manufacture of the monitoring syringe may be those typical in medical applications. Plastics such as polycarbonate may be utilized for the syringe housing and plunger. The band or gradation may be printed directly on the plunger shaft, or may be printed on a discrete plastic sheet or sheath that may then be affixed to the plunger shaft. Various types of printing may be utilized to change the translucency or opacity of the band or gradation. In some embodiments, the type of printing may be based on the type of light to be received by the sensors. For example, carbon-based printing may be utilized for sensors that detect infrared light. Thus, the band or gradation may be utilized as the filter described above.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured all such modifications as fall within the spirit and scope of the technology. Accordingly, what is desired to be secured by Letters Patent is the technology as defined and differentiated herein, and all equivalents.

What is claimed is:

1. An apparatus comprising:
   a syringe housing;
   a plunger comprising a longitudinal axis along a length of the plunger and slidably received within the syringe housing between a first position and a second position, the plunger comprising a substantially opaque portion and a substantially translucent portion, and wherein the substantially translucent portion is substantially translucent through the axis of the plunger;
   a light sensor module disposed on the syringe housing, wherein the light sensor module comprises a light sensor housing having at least a first sensor element and a second sensor element; and
   a light emitter module having a first light emitter and disposed on the syringe housing on a side of the axis opposite the light sensor module, wherein positioning the plunger at the first position aligns the substantially translucent portion with the first sensor element and positioning the plunger at the second position aligns the substantially translucent portion with the second sensor element, and wherein light emitted from the light emitter module passes through the syringe housing and the substantially translucent portion of the plunger as the plunger slides within the syringe housing.

2. The apparatus of claim 1, further comprising a lead extending from the light sensor module.

3. The apparatus of claim 2, further comprising an interface for connecting the lead to a measuring device, and wherein the measuring device displays a total volume injected and emits a warning of a critical outcome.

4. The apparatus of claim 1, wherein the light sensor housing is releasably fixed to the syringe housing.

5. The apparatus of claim 4, further comprising a securement element for releasably securing the light sensor housing to the syringe housing.

6. The apparatus of claim 5, wherein the securement element comprises at least one of a clamp, a clasp, a hook and loop fastener, and a magnet.

7. The apparatus of claim 1, wherein the light emitter module further comprises a light emitter housing and a second emitter element, wherein the first emitter element and the second emitter element are disposed within the emitter housing.

8. The apparatus of claim 7, wherein positioning the plunger at the first position aligns the substantially translucent portion with the first emitter element and positioning the plunger at the second position aligns the substantially translucent portion with the second emitter element.

9. The apparatus of claim 8, wherein the first emitter element and the first sensor element are aligned.

10. The apparatus of claim 7, wherein the light sensor housing is disposed on the syringe housing such that light emitted from the light emitter housing passes through the syringe housing and into the light sensor housing.

\* \* \* \* \*